(12) United States Patent
Lennerstrand et al.

(10) Patent No.: US 7,087,375 B1
(45) Date of Patent: Aug. 8, 2006

(54) METHOD FOR DETERMINING THE MECHANISM OF HIV RT INHIBITORS

(76) Inventors: Johan Lennerstrand, 35 Harvey Goodwin Gardens, Cambridge (GB); Brendan Larder, Monona 6, Churchlane, Cambridge, CB3 7HQ (GB)

( * ) Notice: Subject to any disclaimer, the term of this patent is extended or adjusted under 35 U.S.C. 154(b) by 0 days.

(21) Appl. No.: 09/599,877

(22) Filed: Jun. 23, 2000

(51) Int. Cl.
 *C12Q 1/70* (2006.01)
(52) U.S. Cl. .................. 435/5; 424/188.1; 424/208.1
(58) Field of Classification Search .................. 435/5; 424/188.1, 208.1
 See application file for complete search history.

(56) References Cited

U.S. PATENT DOCUMENTS

| | | | | |
|---|---|---|---|---|
| 5,985,215 A | 11/1999 | Sakazume et al. | ............ | 422/67 |
| 6,046,056 A | 4/2000 | Parce et al. | ................. | 436/514 |

FOREIGN PATENT DOCUMENTS

| | | |
|---|---|---|
| WO | WO 99/30154 | 6/1999 |
| WO | WO 99/67639 | 12/1999 |

OTHER PUBLICATIONS

Ekstrand, D. H. L., et al., 1996, "A sensitive assay for the quantification of reverse transcriptase activity based on the use of carrier-bound template and non-radioactive-product detection, with special references to human-immunodeficiency-virus isolation", Biotechnol. Appl. Biochem. 23:95-105.*
Meyer, P. R., et al., 1999, "A mechanism of AZT resistance: an increase in nucleotide-dependent primer unblocking by mutant HIV-1 reverse transcriptase", Mol. Cell 4:35-43.*
Arion, D., et al., 1998, "Phenotypic mechanism of HIV-1 resistance to 3'-Azido-3'-deoxythymidine (AZT): increased polymerization processivity and enhanced sensitivity to pyrophosphate of the mutant view reverse transcriptase", Biochem. 37:15908-15917.*
Ueno, T., et al., 1995, "Enzymatic characterization of human immunodeficiency virus type 1 reverse transcriptase resistant to multiple 2',3'-dideoxynucleoside 5'-triphosphates", J. Biol. Chem. 270(4):23605-23611.*
Larder, B. A. and D. K. Stammers, 1999, "Closing in on HIV drug resistance", Nature Struct. Biol. 6(2):103-106.*
Larder, B. A. et al., 1999, "A family of insertion mutations between codons 67 and 70 of human immunodeficiency virus type 1 reverse transcriptase confer multinucleoside analog resistance", Antimicrob. Agents Chemother. 43(8):1961-1967.*
Kellam, P, et al., 1992, "Fifth mutation in human immunodeficiency virus type 1 reverse transcriptase con tributes to the development of high-level resistance to zidovudine", Proc. Natl. Acad. Sci. USA 89:1934-1938.*
Arion et al., "Phenotypic Mechanism of HIV-1 Resistance to 3'-Azido-3'-Deoxythymidine (AZT): Increased Polymerization Procesivity and Enhanced Sensitivity to Pyrophosphate of the Mutant Viral Reverse Transcriptase," *Biochemistry*, 37, pp. 15908-15917 (1998).
Canard et al., "Enhanced Binding of Azidothymidine-Resistant Human Immunodeficiency Virus 1 Reverse Transcriptase to the 3'-Azido-3'-Deoxythymidine 5'-Monophosphate-terminated Primer," *The Journal of Biological Chemistry*, vol. 273, 23, pp. 14596-14604 (1998).
Carroll et al., "Sensitivity of HIV-1 Reverse Transcriptase and Its Mutant to Inhibition by Azidothymidine Triphosphate," *Biochemistry*, 33, pp. 2113-2120 (1994).
Coffin, J.M., "HIV Population Dynamics in Vivo: Implications for Genetic Variation, Pathogenesis, and Therapy," *Science*, vol. 267 (1995).
Ekstrand et al., "A Sensitive Assa for the Quantification of Reverse Transcriptase Activity Based on the Use of Carrier-Bound Template and Non-Radioactive-Product Detection, with Special Reference to Human-Immunodeficiency-Virus Isolation," vol. 23, pp. 95-105 (1996).
Furman et al., "Phosphorylation of 3'-Azido-3'-Deoxythymidine and Selective Interation of the 5'-Triphosphate with Human Immunodeficiency Virus* Reverse Transcriptase," *Proc. Natl. Acad. Sci. USA*, vol. 83, pp. 8333-8337 (1986).
Harada et al., "Infection of HTLV-III/LAV in HTL-1-Carrying Cells MT-2 and MT-4 and Application in a Plaque Assay," *Science*, vol. 229, pp. 563-567 (1985).
Harrigan et al., "Significance of Amino Acid Variation at Human Immunodeficiency Virus Type 1 Reverse Transcriptase Residue 210 for Zidovudine Susceptibility," *Journal of Virology*, vol. 70, No. 9, pp. 5930-5934 (1996).

(Continued)

*Primary Examiner*—J. S. Parkin
(74) *Attorney, Agent, or Firm*—Yunling Ren (57) ABSTRACT

The present invention is directed to the field of HIV resistance to RT inhibitors and methods of determining the levels and mechanisms of action of HIV resistance. The methods of the present invention may be accomplished using a novel in vitro assay that provides a reaction well comprising a template for an HIV RT enzyme, a primer, a detectable dNTP substrate, an HIV RT inhibitor, and a ribonucleotide chosen from ATP and GTP or a pyrophosphate. The RT activity is determined by measuring the amount of the detectable dNTP substrate that is incorporated into the template, and the level and/or mechanism of resistance of HIV to the HIV RT inhibitor is determined using the RT activity. The methods may also be used for designing new therapies, screening for new drugs and treatments, and determining the role of mutations in observed resistance.

16 Claims, 3 Drawing Sheets

OTHER PUBLICATIONS

Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents and Chemotherapy*, vol. 42, 2, pp. 269-276 (1998).

Huang et al., "Structure of a Covalently Trapped Catalytic Complex of HIV-1 Reverse Transcriptase: Implications for Drug Resistance," *Science*, vol. 282, pp. 1669-1675 (1998).

Kellam et al., "Recombinant Virus Assay: A Rapid, Phenotypic Assay for Assessment of Drug Susceptibility of Human Immunodeficiency Virus Type 1 Isolates," *Antimicrobial Agents and Chemotherapy*, vol. 38, 1, pp. 23-30 (1994).

Kellam et al., "Fifth Mutation in Human Immunodeficiency Virus Type 1 Reverse Transcriptase Contributes to the Development of High-Level Resistance to Zidovudine," *Proc. Natl. Acad. Sci. USA*, vol. 89, pp. 1934-1938 (1992).

Krebs et al., "Single-Step Kinetics of HIV-1 Reverse Transcriptase Mutants Responsible for Virus Resistance to Nucleoside Inhibitors Zidovudine and 3-TC," *Biochemistry*, 36, pp. 10292-10300 (1997).

Lacey et al., "Biochemical Studies on the Reverse Transcriptase and Rnase H Activities from Human Imunodeficiency Virus Strains Resistant to 3' -Azido-3' deoxythymidine*," *The Journal of Biological Chemistry*, vol. 267, 22, pp. 15789-15794 (1992).

Larder et al., Multiple Mutations in HIV-1 Reverse Transcriptase Confer High-Level Resistance to Zidovudine (AZT), *Science*, vol. 246, pp. 1155-1158 (1989).

Larder et al., "A Family of Insertion Mutations Between Codons 67 and 70 of Human Immunodeficiency Virus Type 1 Reverse Transcriptase Confer Multinucleoside Analog Resistance," *Antimicrobial Agents and Chemotherapy*, vol. 43, No. 8, p. 1961-1967 (1999).

Larder et al., "Quantitative Detection of HIV-1 Drug Resistance Mutations by Automated DNA Sequencing," *Nature*, vol. 365, pp. 671-675 (1993).

Larder et al., "Related Functional Domains in Virus DNA Polymerases," *The EMBO Journal*, vol. 6, 1, pp. 169-175 (1987).

Lardner et al., "HIV with Reduced Sensivity to Zidovudine (AZT) Isolated During Prolonged Therapy," *Science*, vol. 243, pp. 1731-1734 (1989).

Lennerstrand et al., "Application of a Chain Termination Assay for Characterization of Reverse Transcriptase from AZT-Resistant HIV Isolates," *Antiviral Chemistry & Chemotherapy*, vol. 7, 6, pp. 313-320 (1996).

Meyer et al., "A Mechanism of AZT Resistance: An Increase in Nucleotide-Dependent Primer Unblocking by Mutant HIV-1 Reverse Transcriptase," *Molecular Cell*, vol. 4, pp. 35-43 (1999).

Ren et al., "3' -Azido-3'Deoxythymidine Drug Resistance Mutations in HIV-1 Reverse Transcriptase can Induce Long Range Conformational Changes," *Proc. Natl. Acad. Sci. USA*, vol. 95, pp. 9518-9523 (1998).

Schinazi et al., "Mutations in Retroviral Genes Associated with Drug Resistance," *International Antivitarl News*, vol. 5, 8, pp. 129-142 (1997).

Shao et al., "A Non-Radioactive Microtitre Plate Reverse Tranascriptase (RT) Assay, Based on Immobilized Template, for Screening of RT Activity Inhibitors and Evaluation of their Mode of Action," *Antiviral Chemistry and Chemotherapy*, vol. 8, 2, pp. 149-159 (1997).

Shirasaka et al., "Emergence of Human Immunodeficiency Virus Type 1 variants with Resistance to Multiple Dideoxynucleosides in Patients Receiving Therapy with Dideoxynucleosides," *Proc. Natl. Acad. Sci. USA*, vol. 92, pp. 2398-2402, (1995).

Stammers et al., "Crystals of HIV-1 Reverse Transcriptase Diffracting to 2.2 Å Resolution," *J. Mol. Biol.*, vol. 242, pp. 586-588 (1994).

Ueno et al., "Enzymatic Characterizaton of Human Immunodeficiency Virus Type 1 Reverse Transcriptase Resistant to Multiple 2',3' -Dideoxynucleoside 5' -Triphosphates*," *The Journal of Biological Chemistry*, vol. 270, 40, pp. 23605-23611 (1995).

Winters et al., "A 6-Basepair Insert in the Reverse Transcriptase Gene of Human Immunodeficiency Virus Type 1 Confers Resistance to Multiple Nucleoside Inhibitors," *The Journal of Clinical Investihgation*, vol. 102, 10, pp. 1769-1775 (1998).

* cited by examiner

METHOD FOR DETERMINING THE MECHANISM OF HIV RT INHIBITORS

The present invention is directed to the field of HIV resistance to RT inhibitors and methods of determining the levels and mechanisms of action of HIV resistance. More particularly, the present invention relates to a method for investigating resistance of HIV to an RT inhibitor, including determining the level of resistance, the mechanism of resistance, and the use of these methods for designing new therapies, screening for new drugs and treatments, and determining the role of mutations in observed resistance.

To date, the development of treatments in the fight against the HIV virus has focused on preventing viral replication by intervening in reverse transcription (reverse transcriptase inhibitors (RTI)) and viral assembly (protease inhibitors (PI)). RT inhibitors, for example, may block viral replication in various ways, while PI's bind to the active site of the viral protease enzyme, thereby inhibiting the cleavage of precursor poly proteins necessary to produce the structural and enzymatic components of infectious virons.

One type of RT inhibitor, Nucleoside Reverse Transcriptase Inhibitors (NRTIs), compete with the natural nucleoside triphosphates for incorporation into elongating viral DNA by reverse transcriptase. Chemical modifications that distinguish these compounds from natural nucleosides result in DNA chain termination events. NRTIs that are currently available include zidovudine (AZT), didanosine (ddI), zalcitabine (ddC), stavudine (d4T), lamivudine (3TC) and abacavir (ABC).

For example, AZT, which was one of the first HIV RT inhibitors identified, is converted to the triphosphate (TP) by cellular kinases. HIV-1 RT is subsequently able to use AZT-TP as an efficient alternative substrate in the building of the viral DNA. However, AZT-TP lacks a 3'OH necessary for further DNA elongation, thereby causing termination of the growing DNA chain following incorporation. Furman, P. et al, *Proc. Nat.l Acad. Sci.* USA 83, 8333–8337 (1986). Unfortunately, as explained below, resistance to AZT commonly develops during therapy due to rapid virus turnover and the fact that HIV-1 RT is an error prone polymerase. Coffin J. M., *Science* 267, 483–489 (1995); Larder, B. A.& Kemp, S. D., *Science* 246, 1155–1158 (1989); and Larder, B. A., et al., *Science* 243, 1731–1734 (1989) In fact, the development of resistance is seen for all HIV-1 inhibitors currently in clinical use.

Viral drug resistance may develop in any patient treated with sub-optimal antiretroviral therapy or alternatively a patient may be infected with a drug-resistant strain of HIV. Any situation which permits viral replication in the presence of an inhibitor sets the stage for selection of resistant variants. More specifically, retroviruses such as HIV have no proof-reading mechanisms when synthesizing new nucleic acids strands. Errors that occur in the process of incorporating nucleotides during chain elongation are not corrected. This allows for the continuous generation of a number of genetic variants in a replicating viral population. The estimates are that there are $3 \times 10^{-5}$ mutations per nucleotides per HIV replication cycle and the type of substitution mutation is of course random at any one location.

Consequently, given the frequency of the errors and the high rate at which the virus replicates, virtually all possible genetic changes are likely to be generated within a very short time period. More importantly, the genetic changes may alter the configuration of the RT and protease molecules in such a way that they are no longer susceptible to inhibition by the compounds that have been developed to target them.

If antiretroviral therapy is ongoing and if viral replication cannot be completely suppressed, the selection of such genetic variants is inevitable. The viral population will become resistant to the drug(s) administered. Clearly, effective suppression of the viral population is vital to effective treatment.

Viral drug resistance can be defined as any change in the virus that improves replication in the presence of an inhibitor. HIV-1 drug resistance was first described in 1989 and involved patients that had been treated with zidovudine monotherapy, which represented the only treatment option at that time. Larder, B. A., et al., *Science* 243, 1731–1734 (1989). Resistance was detected phenotypically in vitro. For a number of patients, the viral isolates required 100-fold higher zidovudine concentrations to inhibit replication to the same extent as pretreatment isolates from the same individual. Subsequently, the genetic basis for zidovudine resistance was characterized.

Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the compounds used. In addition, multi-drug resistance has been documented during combination therapy. Shirasaka, T. et al., *Proc. Natl. Acad. Sci. USA* 14, 2398–2402 (1995); Larder, B. A., et al., *Antimicrob. Agents Chemother.* 43, 1961–1967 (1990). For example, resistance development has been observed with the introduction of dual NRTI combination therapy as well as during the administering of the more potent NNRTIs and Pls.

Extensive genetic analysis of resistant viral isolates generated through in vivo or in vitro selection has revealed that resistance is generally caused by mutations altering the nucleotide sequence at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled. See Schinazi, R. F., Larder, B. A. & Meliors, J. W. 1997. *Int. Antiviral News.* 5, 129–142 (1997). Additionally, an electronic listing with mutations has also become available on the internet at sites such as hiv-web.lanl.gov or www.viralresistance.com. Of course, as antiretroviral drugs are administered for longer periods of time, mostly in combination with each other, and as new antiretrovirals are being developed and added to the present drugs, new resistance-correlated genetic variants are being discovered. Of particular import is that the combination of antiretroviral agents can influence resistance characteristics.

It should be noted that the degree of susceptibility of a genetic variant to an antiretroviral compound is expressed herein relative to the wild-type virus (HIV III/B/LAI reference sequence) as found, for example, in GenBank, the sequence of which is hereby incorporated by reference. Susceptibilities are generally expressed as ratios of $IC_{50}$ or $IC_{90}$ values (the $IC_{50}$ or $IC_{90}$ value being the drug concentration at which 50% or 90% respectively of the viral population is inhibited from replicating). Additionally, the genetic mutation is normally written as in reference to the wild type virus, i.e., K101N refers to replacement of a Lysine at codon 101 with a Asparagine. However, the mutations of the invention do not depend on the wild-type example listed in order to be within the practice of the invention. For example, the mutation 101N, refers to an Asparagine at the 101 codon regardless of the whether there was a Lysine at 101 prior to mutation.

Figure 1:
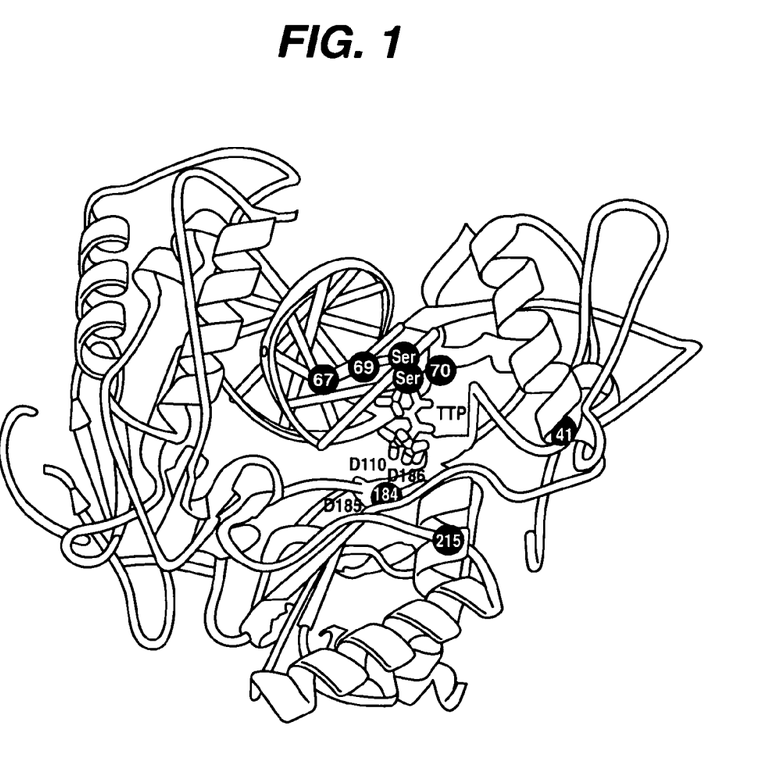
FIG. 1 is a diagram of part of the HIV-1 RT, which shows template/primer, TTP and positions of certain drug resistance mutations within the p66 subunit. Some of the mutated residues that give AZT resistance 41,67,69,70,215 and 219 are shown as spheres. The Ser—Ser insertion after position 69 is also shown. The region of double-stranded DNA is indicated by spikes between template and primer. The polymerase active site catalytic aspartate residues, 110,185 and 186, are also shown.

Analysis of AZT resistant HIV-1 strains from patients has resulted in the identification of several mutations in the RT coding sequence. For example, changes at codons 41, 67, 70, 210, 215 and 219 result in specific resistance to AZT and not to other currently used nucleoside analogs. Larder, B. A.& Kemp, S. D., *Science* 246, 1155–1158 (1989); Harrigan, P. R., et al. *J. Virol.* 70, 5930–5934 (1996); Kellam, P. et al., *Proc. Natl. Acad. Sci. USA* 89, 1934–1938 (1992). These mutations can cause the virus to become highly resistant to AZT (in some combinations over a 100-fold increase in $IC_{50}$ value). However, the biochemical mechanism of resistance conferred by these mutations has remained a puzzle since only minor or no differences were seen by comparing in vitro the kinetic properties of mutant enzymes with the kinetic properties of wild type enzymes in the presence of different AZT-TP concentrations. Lacey, S. F. et al. *J. Biol. Chem.* 267, 15789–15794(1992); Carroll, S. S. et al., (1994) *Biochemistry* 33, 2113–2120 (1994); Lennerstrand J. et al., Antiviral Chem. Chemother. 7(6), 313–320 (1996); Krebs, R. et al., *Biochemistry* 36, 10292–10300 (1997). In addition, while there are pieces of evidence, the overall picture of the mechanism is still very uncertain. For example, a different set of RT mutations, i.e. A62V, V75I, F77L, F116Y and Q151M, which confer multi nucleoside analog resistance (where Q151M is the key mutation), did show decreased binding of AZT-TP and correlated with virus data. Ueno, T., et al., J. Biol. Chem. 270, 23605–23611 (1995). Moreover, structural studies of catalytic HIV-1 RT complexes indicate that while many resistance mutations for the "ddN" NRTIs such as ddC, ddI and 3TC are sufficiently close to the dNTP (deoxynucleotide triphosphate) binding site to exert direct effects on inhibitor binding, many other AZT resistance mutations are more distal to the active site (FIG. 1). Huang H. et al., Science 282, 1669–1675 (1998). On explanation is that long range conformational changes propagated from mutations at 215 and 219 to the active site have been observed for the D67N, K70R, T215F, K219Q mutant HIV-1 RT. Ren, J. et al., *Proc. Natl. Acad. Sci. USA* 95, 9518–9523 (1998).

Recently, other novel biochemical mechanisms for AZT resistance have been proposed. Arion et al showed that enhanced removal of AZT-MP (AZT-monophosphate) from blocked primers could occur for an AZT resistant mutant compared to wild type RT. This was due to pyrophosphate (PPi)-depended pyrophosphorolysis, the reverse reaction of DNA synthesis. Arion, D. et al., *Biochemistry* 37, 15908–15917 (1998). Likewise, Meyer et al has shown a ribonucleotide (ATP or GTP)-depended primer unblocking reaction that produces dinucleoside polyphosphate. Meyer, P. R. et al., *Mol. Cell* 4, 35–43 (1999). Both of these studies were performed with HIV-1 RT having mutations at codons D67N, K70R, T215F, and K219Q. However, while an increase in AZT-TP resistance of up to five times was demonstrated with this mutant using physiological concentrations of either PPi or ATP, the difference does of course not fully correlate to the 100-fold increase in $IC_{50}$ for AZT observed with the virus.

In addition to assays for determining the mechanism of HIV resistance to RT inhibitors, there is also a need for simple in vitro methods of determining the level of resistance of a strain or mutant HIV to RT inhibitors. While phenotypic testing directly measures the actual sensitivity of a strain of HIV to a particular therapeutic agent, phenotypic testing can be quite time intensive and is generally quite expensive. Moreover, most in vitro tests of the kinetic properties of mutant enzymes demonstrate little or no correlation to the levels of resistance observed with viral phenotypic assays.

In view of the prevalence of viral resistance, and its role in therapy failure, an understanding of the mechanism of viral resistance is vital. For example, a more complete understanding of viral resistance and its mechanism of action, including the effects of mutations at specific codons, is important in the development of new antiviral treatments, new drugs and new combination therapies. More specifically, methods of determining mechanisms of viral resistance, the levels of viral resistance and for testing new treatments in order to combat viral resistance are needed.

To achieve these and other advantages, and in accordance with the principles of the present invention as embodied and broadly described herein, the present invention, in one aspect, provides a method for determining the level of resistance of HIV to an HIV RT inhibitor. In one embodiment, the method provides a reaction well comprising a template for an HIV RT enzyme, a primer, a detectable dNTP substrate, an HIV RT inhibitor, and a ribonucleotide chosen from ATP and GTP or a pyrophosphate. An HIV RT enzyme is then added to the reaction well, wherein the HIV RT enzyme incorporates the detectable dNTP substrate or the HIV RT inhibitor into the template. The HIV RT enzyme may be chosen from a wild-type RT enzyme or a mutant RT enzyme. The RT activity is then determined by measuring the amount of the detectable dNTP substrate that is incorporated into the template, and the resistance of HIV to the HIV RT inhibitor is determined from the RT activity.

The invention also provides for a method of designing a therapy for treating HIV comprising determining the resistance of HIV to an HIV RT inhibitor using the method described above, and designing the therapy based on the resistance of HIV to the HIV RT inhibitor.

In another embodiment, the invention provides for a method for designing a therapy for treating HIV, which begins by determining the resistance of HIV to an HIV RT inhibitor using the method described above. The method is then repeated with the reaction well further containing a second HIV RT inhibitor and the change in RT activity that is caused by the addition of the second HIV RT inhibitor is determined. The new therapy is then designed based on the change in RT activity due to the addition of the second HIV RT inhibitor.

The invention also provides for a kit for determining the level of resistance of HIV to an HIV RT inhibitor. The kit of the invention may comprise a template for an HIV RT enzyme; a primer, a detectable dNTP substrate; and a ribonucleotide chosen from ATP and GTP or a pyrophosphate. The kit may further comprise a mutant RT enzyme.

Also within the practice of the invention is a method for determining the mechanism of action of an HIV RT inhibitor comprising: providing a reaction well that contains at least one template for an HIV RT enzyme; at least one primer; at least one detectable dNTP substrate; at least one HIV RT inhibitor; and at least one ribonucleotide chosen from ATP and GTP or at least one pyrophosphate. An HIV RT enzyme chosen from a wild-type RT enzyme or a mutant RT enzyme is then added to the reaction well. The HIV RT enzyme incorporates the detectable dNTP substrate or the HIV RT inhibitor into the template. The RT activity is subsequently determined by measuring the amount of the detectable dNTP substrate incorporated into the template, and the mechanism of action of the HIV RT inhibitor is determined from the RT activity.

In another embodiment, the invention provides a method for determining the effect of at least one mutation in an HIV RT enzyme on the resistance of HIV to an HIV RT inhibitor comprising providing a reaction well that contains a template for an HIV RT enzyme; a primer; a dNTP substrate; an HIV RT inhibitor; and at least one ribonucleotide chosen from ATP or GTP or at least one pyrophosphate. An HIV RT enzyme is then added to the reaction well such that the HIV RT enzyme incorporates the detectable dNTP substrate or the HIV RT inhibitor into the template. The RT activity is subsequently determined by measuring the amount of the detectable dNTP substrate incorporated into the template. The previous steps are then repeated in a new reaction well in which the HIV RT enzyme is a mutant RT enzyme and the RT activity in the different reaction well are compared. The effect of the mutation on the resistance of HIV to an HIV RT inhibitor is subsequently determined based on this comparison.

It is to be understood that both the foregoing general description and the following detailed description are exemplary and explanatory only and are not restrictive of the invention, as claimed. Further features and/or variations may be provided in addition to those set forth herein. For example, the present invention may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated in and constitute a part of this specification, illustrate various embodiments and/or features of the invention and together with the description, serve to explain the principles of the invention. In the drawings:

FIG. 2 is the fold resistant data from Table 3. The RT AZT-TP inhibition assay data are the $K_i/K_m$ ratios of the values divided by the equivalent ones for wild type (HXB2) RT. The HIV drug susceptibility assay levels of resistance values are based on the $IC_{50}$ relative to the wild type HXB2 virus control.

FIG. 3 is the fold resistant data from Table 4. The RT d4T-TP inhibition assay data are the $K_i/K_m$ ratios of the values divided by the equivalent ones for wild type (HXB2) RT. The HIV drug susceptibility assay levels of resistance values are based on the $IC_{50}$ relative to the wild type HXB2 virus control.

DETAILED DESCRIPTION OF THE INVENTION

Reference will now be made in detail to the presently preferred embodiments of the invention. The invention, in one aspect provides a method for determining the level of resistance of HIV to an HIV RT inhibitor. The methods of the present invention may be accomplished using a novel in vitro assay, herein referred to as the RT assay. In one embodiment, the assay provides a reaction well comprising a template for an HIV RT enzyme, a primer, a detectable dNTP substrate, an HIV RT inhibitor, and a ribonucleotide chosen from ATP and GTP or a pyrophosphate. An HIV RT enzyme is then added to the reaction well, wherein the HIV RT enzyme incorporates the detectable dNTP substrate or the HIV RT inhibitor into the template. In another embodiment of the invention, the HIV RT enzyme is present in a reaction well and the template, primer, detectable dNTP substrate, HIV RT inhibitor, and ribonucleotide or pyrophosphate are added to the HIV RT enzyme. The HIV RT enzyme may be chosen from a wild-type RT enzyme or a mutant RT enzyme. The RT activity is then determined by measuring the amount of the detectable dNTP substrate that is incorporated into the template, and the level of resistance of HIV to the HIV RT inhibitor is determined using the RT activity. These methods may also be used to elucidate the biochemical mechanism of HIV resistance.

In one embodiment, the assay is an enzymatic kinetics assay and the level of resistance of HIV to the HIV RT inhibitor and/or the mechanism of HIV resistance is determined from the kinetics of binding of the RT inhibitor and/or the kinetics of RT inhibitor inhibition using a wild type HIV RT or mutant RT protein. For example, the Michaelis constant, $K_m$, and the dissociation constant of the enzyme-inhibitor complex, $K_i$, may be determined by fitting the data at various concentrations of substrate, RT inhibitor, and/or other reagents, to the Michaelis-Menten competitive inhibition equation. The degree of resistance may then be expressed as $K_i/K_m$. Any other kinetic analysis known in the art may be utilized with the methods of the invention depending on the application envisaged.

The in vitro methods of the present invention provide benefits and advantages not found in previous methods and assays for investigating HIV resistance. For example, until recently, no obvious differences had been found to explain the magnitude of resistance seen in cell culture assays when $K_i$ values for AZT-TP for wild type and mutant RTs were compared. Lacey, S. F. et al. *J. Biol. Chem.* 267, 15789–15794(1992); Carroll, S. S. et al., (1994) *Biochemistry* 33, 2113–2120 (1994); Lennerstrand J. et al., Antiviral Chem. Chemother. 7(6), 313–320 (1996); Krebs, R. et al., *Biochemistry* 36, 10292–10300 (1997). Unidentified cellular factors were one of the many suggestions that were involved in this mechanism. Recently, enhanced binding of an AZT resistant RT to AZT-MP terminated primer was observed and it was subsequently suggested that pyrophosphorolysis was involved in enhanced removal AZT-MP from terminated primers with AZT mutant RT. Canard B. et al., *J. Biol. Chem.* 273, 14596–14604 (1998). This was seen with PPi at intracellular concentration (150 µM), causing enhanced pyrophosphorolysis, or with NTPs (ATP or GTP at 3.2 mM) causing enhanced dinucleoside polyphosphate synthesis. Arion, D. et al., *Biochemistry* 37, 15908–15917 (1998); Meyer, P. R. et al., *Mol. Cell* 4, 35–43 (1999). However, although the virus strains used were highly resistant (100-fold) in culture (RTs with mutations at codons D67N, K70R, T215F and K219Q), the in vitro assays utilized only detected a minor difference in resistance using either PPi (3-fold higher $IC_{50}$ for AZT-TP) or ATP (5-fold higher dinucleotide polyphosphate synthesis). Furthermore, in one case a significant effect was only observed with ATP and GTP but not with added PPi.

One of the advantages of the methods of the present invention, however, is their ability to reproduce the cell culture or phenotypic data more accurately. The present invention may be utilized to investigate the level of HIV resistance and the mechanism of HIV resistance by measuring the binding constants in a sensitive RT inhibitor assay. More importantly, the methods do not require the natural substrate or sequence of template-primer. The invention demonstrates that these are not important for accurately investigating the levels and mechanism of HIV resistance to an RT inhibitor. In other words, the invention provides an in vitro, fast, and inexpensive method for analyzing HIV resistance to RT inhibitors and accurately determining the level of HIV resistance without the need for cell culture or other phenotypic assays.

The methods of the invention are especially applicable in high throughput testing or evaluation devices. For example, the number of mutations and combinations of mutations in the viral genome of HIV that may confer drug resistance is enormous. Therefore, it is crucial to be able to determine the level of resistance and investigate the mechanism of resistance for a large number of mutations and/or a large number of RT inhibitors in a quick, efficient manner. As described above, cell culture and/or phenotypic experiments do not always offer these advantages. It is within the practice of the invention, however, to prepare a sample rack or solid support made up of numerous reaction wells, such that each reaction remains isolated form one another. Simultaneous transfer of one or more reagents to the reaction wells may then be achieved by one of the many techniques used in the art of high throughput analysis.

One or more of the contents of each of the reaction wells may be varied. For example, in one embodiment, each reaction well contains a template for an HIV RT inhibitor, a primer, a detectable dNTP substrate and a ribonucleotide chose from ATP or GTP of a pyrophosphate. However, a different HIV RT enzyme chosen from a wild-type RT enzyme or a mutant RT enzyme is then added to each reaction well. The reaction wells may form an array or may employ another means of identifying or addressing each compartment. The RT activity of each reaction well may then be automatically determined from the amount of detectable dNTP substrate incorporated into the template of each reaction well, and recorded. Other embodiments include, but are not limited to varying the concentration of one or more of the components, and using the same mutant RT enzyme and varying the HIV RT inhibitor.

There are numerous methods for handling high throughput. i.e., analyzing a large number of samples in a relatively short period of time. Any method of high throughput analysis available may be applied to the methods of the invention. Examples include, but are not limited to: U.S. Pat. No. 5,985,215 of Sakazume et al., entitled Analyzing Apparatus Having a Function Pipette Samples; U.S. Pat. No. 6,046,056 of Parce et al., entitled High Throughput Screening Assay Systems in Microscale Fluidic Devices; WO 00/14540 of Pauwels et al., entitled Method For the Rapid Screening of Analytes; WO 99/30154 of Beutel et al., entitled Continuous Format High Throughput Screening; and WO 99/67639 of Wada et al., entitled High Throughput Methods, Systems and Apparatus for Performing Cell Based Screening Assays, the disclosures of which are herein incorporated by reference in their entirety.

For example, as described herein, the invention was effective in demonstrating both a PPi dependent pyrophosphorolysis and ribonucleotide (ATP)-dependent mechanism for AZT-TP resistance. Not to be limited as to theory, the methods of the invention may yielded higher magnitudes of resistance because the invention enables the measurement of multiple chain termination events, which should be more reflective of the in vivo situation and could explain why previous assays did not find a similar magnitude of resistance.

In the practice of the invention, any template that would serve as an effective template for an HIV RT enzyme may be used. The template may or may not be bound to the reaction well, but in a preferred embodiment is bound to the reaction well. In a further preferred embodiment the template is chosen from poly-rA or a heteropolymer RNA or DNA. Any primer complementary to the template chosen may be used. In one embodiment, the primers are chosen from oligo-dt or a primer complementary to the heteropolymer template.

Detectable dNTP substrates useful in the practice of the invention include any dNTP substrate, and in a preferred embodiment, any dTTP substrate (deoxythymidine triphosphate), that is detectable before and/or after integration into the template. Detectable dNTP substrates include but are not limited to a radioactive labeled dTTP or any radioactive labeled dNTP, and a dNTP substrate that is capable of being detected by fluorescence, luminescence, or absorption spectrometry. The detectable dNTP substrate may be detectable on its own or it may bind to a tracer, which may then be detected. The tracer may be an optical tracer, such as a tracer that may be detected by fluorescence, luminescence, or absorption spectrometry, or the tracer may be a radioactive labeled tracer. In one embodiment, the detectable dNTP substrate is bromo-deoxyuridine-triphosphate and the optical tracer is an antibody or a monoclonal antibody such as monoclonal anti-BrdU antibody, conjugated to alkaline phosphatase that binds to the dNTP substrate.

HIV RT inhibitors for use in the practice of the invention include any nucleoside or nucleoside analog which acts as an RT inhibitor including the triphosphate analog of an RT inhibitor. RT inhibitors useful in the practice of the invention include but are not limited to known RT inhibitors such as AZT, 3TC, ddI, ddC, d4T, abacavir and their triphosphate analogs such as AZT-TP and d4T-TP. HIV RT inhibitors that may be used in the methods of the invention also include experimental drugs or newly designed or synthesized drugs or natural products. The HIV RT inhibitor may also be combination therapies containing known and/or experimental HIV RT inhibitors, treatments or drugs.

The reaction well of the invention may also include at least one ribonucleotide chosen from ATP and GTP or at least one pyrophosphate. The effects of one or more of these compositions or combinations of ribonucleotides and/or pyrophosphates on HIV resistance may also be examined within the practice of the invention. The concentrations of ribonucleotides and pyrophosphates may be varied depending on the application envisaged. For example, the influence of pyrophosphate (together with ATP) in vivo obviously depends on the intracellular concentrations. In a preferred embodiment, the intracellular concentrations, which are well established at 3.2+/1.5 mM for ATP, 0.5+/−0.2 mM for GTP, and 130 µM for pyrophosphate are used.

The methods of the invention may be initiated by adding to the reaction well an HIV RT enzyme. The HIV RT enzyme may be a wild-type enzyme or a mutant RT enzyme. Any RT enzyme or mutant RT enzyme that may incorporate the detectable dNTP substrate and/or the HIV RT inhibitor into the template may be useful in the practice of the invention.

In another embodiment, the invention provides a method for determining the effect of at least one mutation in an HIV RT enzyme on the resistance of HIV to an HIV RT inhibitor comprising providing a reaction well that contains a template for an HIV RT enzyme; a primer; a dNTP substrate; an HIV RT inhibitor; and at least one ribonucleotide chosen from ATP or GTP or at least one pyrophosphate. HIV resistance may be studied using a broad panel of mutant RT enzymes or may be used to determine the effect of a mutation or combination of mutations on the mechanism or level of resistance of one or more RT inhibitors. In one embodiment, the methods may be used to determine which mutations are involved in the ATP-mediated effect described herein. Important mutations appear to be located in the fingers domain of RT, specifically in the β2–β3 loop, as alteration at positions 67, 69 and 70. Of particular interest are codon 69 insertion mutations.

In one embodiment, a mutant HIV RT enzyme is added to the reaction well such that the mutant HIV RT enzyme incorporates the detectable dNTP substrate or the HIV RT inhibitor into the template. The RT activity is subsequently determined by measuring the amount of the detectable dNTP substrate incorporated into the template. The previous steps are then repeated in a new reaction well in which the HIV RT enzyme is another mutant RT enzyme or the wild type RT enzyme and the RT activity in the different reaction wells are compared. The effect of the mutation on the resistance of HIV to an HIV RT inhibitor is subsequently determined based on this comparison.

The invention also provides methods for identifying the specific mutations or combinations of mutations involved in HIV resistance. In one embodiment, this is accomplished by comparing binding of an RT inhibitor to a variety of mutant RTs containing combinations of different mutations. For example, the methods of the invention were used to show that some AZT-resistant RTs have decreased AZT-TP binding of up to 20-fold when compared to wild type RT using ATP as the acceptor. A similar but slightly lower effect was also seen with PPi at physiological concentrations. Moreover, using a large panel of mutants, good correlation has been observed between the resistance data at the RT level and corresponding phenotypic, HIV resistance, cell culture data.

As described above, the methods of the invention, which also may be referred to as enzymatic kinetics assays, are less expensive and easier to use than a cell culture phenotypic or drug susceptability assay. Using the in vitro assay or methods of the invention, one could investigate the potential resistance mechanism of any nucleoside analog and/or screen for small molecules that block this mechanism. The invention also provides for a method of designing a therapy for treating HIV comprising determining the resistance of HIV to an HIV RT inhibitor using the methods described herein, and subsequently designing a therapy based on the resistance of HIV to the HIV RT inhibitor. A therapy may consist of a drug, a combination of drugs, or any other treatment for HIV. In one embodiment, the method for designing a therapy is used to screen for new drugs or drug combinations.

In another embodiment, the invention provides for a method for designing a therapy for treating HIV which begins by determining the resistance of HIV to an HIV RT inhibitor using the method described above. The method is then repeated with the reaction well further containing a second HIV RT inhibitor and the change in RT activity that is caused by the addition of the second HIV RT inhibitor is determined. The therapy is then designed based on the change in RT activity due to the addition of the second HIV RT inhibitor.

The invention also provides for a kit. The kit may be used for any of the methods described herein. However, in a preferred embodiment, the kit may be used to determine the level of resistance of HIV to an HIV RT inhibitor. The kit of the invention may comprise a template for an HIV RT enzyme; a primer; a detectable dNTP substrate; and a ribonucleotide chosen from ATP and GTP or a pyrophosphate. The kit may further comprise a mutant RT enzyme and/or a wild type RT enzyme.

The following examples are provided by way of illustration and are not intended to be limiting of the present invention.

EXAMPLE 1

Mechanism of Resistance of HIV-1 to Zidovudine (AZT)

The correlation between viral AZT resistance and resistance to AZT-TP at the enzyme level was demonstrated, including the potential involvement of either a pyrophosphorolysis mechanism or a ribonucleotide dependent analog to pyrophosphorolysis on the inhibition of reverse transcriptase by AZT-TP.

The experiments were conducted by constructing nine HIV-1 RT mutants containing conventional AZT resistance mutations and/or T69S-xx codon insertions. The 3TC resistance mutation M184V was also included in some of these constructs. The choice of mutations was based on those seen in patient samples treated with AZT alone or together with other nucleoside analogs. Mutations were also chosen to study the potential involvement of the RT finger domain. The AZT susceptibility of these mutants relative to wild type HIV virus (HXB2) was studied in both a recombinant virus assay (phenotypic assay) and an enzymatic kinetics assay. The results demonstrate that the methods of the invention were able to elucidate the mechanism of HIV resistance to AZT and were effective at determining the level of HIV resistance that is comparable to the level determined using phenotypic testing.

Site-Directed Mutagenesis of HIV-1 RT.

Single or multiple nucleotide changes were introduced into the RT-coding region of a wild-type HXB2-D EcoRI-NdeI restriction enzyme fragment cloned into the expression vector pKK233-2 (Pharmacia Biotech). Larder, B. A. et al., *EMBO* J. 6, 169–175 (1987). Mutations were generated using commercial site-directed mutagenesis kits; ExSite or QuikChange (Stratagene). The mutated cloned expression vectors were transformed into *E. coli* strain XL1-Blue and the genotypes were verified by DNA sequence analysis. The mutants were initially screened for expression of RT activity in supernatants of *E. Coli* extracts using a standard Lenti-RT activity assay (Cavidi Tech, Sweden), before proceeding to purification of RT protein or to the next site directed mutagenesis step.

DNA Sequence Analysis of HIV-1 RT from Site-Directed Mutants.

PCR products encompassing the RT gene from each site directed mutated clone were generated by nested PCR. These fragments were analyzed by dideoxynucleotide-based sequencing using the Big Dye terminator kit (Applied Biosystems). The sequencing reaction was analyzed on an ABI 377 DNA sequencer. Larder, B. A. et al., *Nature* 365, 671–673 (1993).

Cell Culture HIV Drug Susceptibility Determination (Phenotypic Susceptibility).

The proviral molecular clone pHIV RTBstEII, from which the sequence for RT was deleted, was co-transfected with the RT PCR product (from selected mutant clones) into MT-4 cells as described previously. Kellam P.& Larder B. A.

*Antimicrob. Agents Chemother.* 38, 23–30 (1994); Harada, S. et al., *Science* 229, 563–566 (1985); Hertogs, K. et al., *Antimicrob. Agents Chemother.* 42, 269–276 (1998). Phenotypic susceptibility of these viable recombinant viruses to nucleoside analogs was then determined. Id. Fold resistance values were calculated by dividing the mean 50% inhibitory concentration ($IC_{50}$) for a recombinant virus from a mutant clone by the mean $IC_{50}$ for recombinant wild type virus (HXB2). A preferred phenotypic method for determining HIV drug susceptibility is the Antivirogram™ (Virco, Mechelen, Belgium).

Results of HIV drug susceptibility assay with different nucleoside analogs are summarized in Table 1.

TABLE 1

HIV-1 susceptibility of site-directed mutants to nucleoside analogs.

| Mutations | Fold resistance in $IC_{50}$ relative to HXB2 | | | | | |
|---|---|---|---|---|---|---|
| | AZT | d4T | 3TC | ddI | ddC | Abacavir |
| M41L, T215Y | 26.2 | 2.6 | 1.0 | 0.9 | 2.5 | 4.4 |
| M41L, D67N, K70R, T215Y | 24.1 | 4.1 | 2.5 | 0.9 | 0.8 | 1.4 |
| D67N, K70R | 11.2 | 5.1 | 1.2 | 0.3 | 1.3 | 1.8 |
| M41L, M184V, T215Y | 5.2 | 2.2 | >62 | 8.0 | 5.0 | 7.1 |
| M41L, D67N, K70R, M184V, T215Y | 6.4 | 3.7 | >62 | 2.4 | 5.1 | 4.1 |
| M41L, D67N, K70R, M184V, L210W, R211K, L214F, T215Y | 16.0 | 4.0 | >129 | 8.7 | 7.7 | 10.4 |
| T69S-SS | 2.0 | 4.4 | 5.0 | 4.3 | 3.2 | 3.0 |
| M41L, T69S-SS, T215Y | 12.0 | 7.1 | 4.3 | 2.5 | 1.5 | 4.6 |
| M41L, T69S-SS, L210W, R211K, L214F, T215Y | >67 | 3.3 | 7.4 | 3.4 | 2.4 | 10.3 |
| T69S-SG | 8.1 | 4.4 | 2.9 | 2.1 | 1.7 | 4.0 |
| M41L, T69S-SG, T215Y | >96 | 4.0 | 11.3 | 5.0 | 2.8 | 9.6 |
| M41L, T69S-SG, L210W, R211K, L214F, T215Y | >96 | 8.3 | 20.3 | 4.4 | 4.8 | 12.0 |
| T69S-AG | 7.0 | 6.9 | 4.2 | 3.8 | 2.8 | 7.0 |
| M41L, T69S-AG, T215Y | >96 | 3.1 | 6.1 | 6.5 | 2.5 | 12.0 |
| V75T | 1.4 | 2.7 | 3.2 | 2.5 | 3.0 | 1.8 |
| Q151M | 2.1 | 3.0 | 2.0 | 3.5 | 5.4 | 2.8 |
| M41L, T69S-AG, L210W, R211K, L214F, T215Y | >96 | 17.7 | 10.1 | 6.5 | 3.0 | 13.2 |

The specific mutations created in a HXB2 background are indicated. The fold increase values are calculated with the HIV drug susceptibility assay and represent the mean of at least two separate determinations. The mean $IC_{50}$ for the wild type control virus in these experiments were: AZT, 0.012 µM; d4T, 1.2 µM; 3TC, 0.6 µM; ddI, 1.6 µM; ddC, 0.71 µM; Abacavir, 2.1 µM.

Codons M41L, D67N, K70R, T215Y (designated as 41/67/70/215) showed specific AZT resistance (24-fold increased $IC_{50}$). When these mutations were separated to create constructs with a D67N plus K70R alone and M41L plus T215Y alone, 11- and 26-fold resistance was observed, respectively. A virus with the 3TC mutation, M184V, in a background of AZT mutations showed resensitization to AZT (5–6 fold resistance). With the additional polymorphism's, L210W, R211K and L214F, AZT resistance increased to 16-fold compared with the wild type. The 69 insertions (T69S-XX designated as 69S-XX) which are associated with multi-nucleoside resistance, were investigated either alone, or in the presence of AZT resistance mutations (which is more typically seen in patient samples). Larder, B. A., et al., *Antimicrob. Agents Chemother.* 43, 1961–1967 (1990); Winters, M. A., et al., *J. Clin. Invest.* 102, 1769–1775 (1998). Constructs containing these insertions showed reduced susceptibility to almost all nucleoside analogs (the 69S-SG and -AG mutants alone showed 7–8-fold AZT resistance but no significant resistance was seen with the 69S-SS mutant). By adding different AZT resistance mutations to the background of 69S-SS, a 12- and >111-fold increase in $IC_{50}$ to AZT was seen together with a broader spectrum of multi-nucleoside resistance. Similar variants that were also constructed with 69S-SG or -AG backgrounds gave an even higher level of multi-nucleoside resistance, including high-level AZT resistance (>96-fold).

Expression and Purification of HIV-1 RT.

Expression and purification of RT has been described. Stammers, D. K., et al., (*J. Mol. Biol.* 242, 586–588 (1994). Briefly, RT was expressed in XL1-Blue *E. coli* grown with 50 mg/L kanamycin and ampicillin in 2xTY media for 18 hour at 36° C. and in presence of 100 µg/L isopropyl-β-D-thiogalactopyranoside (IPTG) for 6 hours. After sonication of extracts containing the enzyme, purification was performed by ion exchange chromatography in several steps using both 50 HQ and 50 HS columns (PerSeptive Biosystems). The final RT products, in a heterodimeric form (p66/p51), had a purity of >90% by SDS PAGE and had specific activity of 1400–3500 U/mg as defined by the standard Lenti RT assay (Cavidi Tech, Sweden).

Novel RT Assay

Cavidi Tech (www.cavidi.com) provided the Lenti RT assay separate kit components adaptable for biochemical inhibitory studies. The principle, performance and composition of this non-radioactive microtitre plate RT assay has been described. Ekstrand, D. H., et al., *Biotechnol. Appil. Biochem.* 23, 95–105 (1996); Shao X., et al., *Antiviral Chem. Chemother.* 8(2), 149–159 (1997). The assay components used in this study for the RT activity step were (i) RT reaction buffer (final concentrations in 200 µl/well); Hepes, 10 mM, pH 7.6; oligo $(dT)_{22}$, 1.25 ng/ml; $MgCl_2$, 5 mM; dextran sulfate, 0.05 g/L; spermine, 2 mM; Triton X-100, 0.5% (v/v); EGTA, 0.2 mM; BSA, 0.5 mg/ml. (ii) Template; i.e. 96-well microtitre plates with solid phase-conjugated polyadenylic acid (polyrA), 40 ng/well. (iii) Substrate dNTP; separately lyophilized BrdUTP. Extra chemicals for novel application to the methods of the invention were ATP and GTP (Pharmacia Biotech) and sodium pyrophosphate (PPi) (Sigma).

The RT assay was conducted by pre-incubating 175 µl/well reaction buffer with BrdUTP and AZT-TP (Moravek Biochemicals, CA, USA) in presence or absence of either 1.5, 3.2 or 6 mM ATP (when added as solution the pH was adjusted to 7.6 with NaOH), 0.5 mM GTP or 150 µM PPi. Examples of BrdUTP and AZT-TP concentrations used for $K_m$ and $K_i$ determinations are given below and in Table 2. After the preincubation, 30 minutes at 33° C., the RT reaction was started by addition of 25 µl purified RT mutants/wild type enzyme diluted to 5–25 pM; 0.2–2 mUnits/well. The RT reaction proceeded for 3 h at 33° C. and was terminated by washing of the plate.

In the next step, 100 µl/well tracer buffer (alkaline phosphate(AP)-conjugated anti-BrdU-antibody) was incubated for 90 min at 33° C. and stopped with new wash. Finally, the RT activity was measured as the amount of conjugated antibodies bound to the BrdU incorporated to solid bound template by adding AP substrate buffer (200 μl/well) and reading the color change at Abs 405 nm/h. The Abs 405 nm, with reference wavelength of 630 nm, was read at different times and background was subtracted.

The potential for PPi contamination in the ATP reagent was eliminated by treatment with thermostable pyrophosphatase (Boehringer Mannheim). 27 mM ATP was incubated in reaction mixture (600 μl) containing, Hepes, 40 mM pH 7.6; KCl, 60 mM; dithiothreitol (DTT) 1 mM; $MgCl_2$, 10 mM; glycerol 2.5% (v/v) and 12 Units Pyrophosphatase. The reaction mixture was incubated for 15 min at 72° C. and stored on ice prior to RT assay (25 μl well) with AZT-TP as described above. As a control for untreated ATP, the ATP was incubated in the same reaction but without pyrophosphatase.

The assay was used to study the kinetics of AZT-TP inhibition with purified wild type and mutant RT protein. The thymidine analog BrdUTP was used as dNTP substrate and when compared to dTTP has been shown to give similar $K_m$ and $V_{max}$ values using wild type RT enzyme in the Lenti RT assay. Ekstrand, D. H., et al., *Biotechnol. Appl. Biochem.* 23, 95–105 (1996). The $K_m$ and $K_i$ values from RT activity AZT-TP assays were obtained by fitting the data to the Michaelis-Menten competitive inhibition equation using the Grafit 4.10 program (Erithacus Software). The $K_m$ values were determined using six different concentrations of BrdUTP from 20 nM to 20 μM in approximately 4 fold increments. The $K_i$ values were determined for AZT-TP using three different AZT-TP concentrations adjusted optimally for each mutant's expected $K_i$ value, as shown in Table 2. The amount of primer used in RT assay was set to 0.25 ng oligo(dT)$_{22}$/well, this was equivalent to the primer's Km value in a 3 hours RT reaction. Reproducible kinetic data ($K_i/K_m$ ratios: +/−10%) was obtained in RT amounts of 3.5–35 pM; 0.2–2.5 mUnits/well. Tested with wild type (HXB2, two batches) and mutant (M41L, D67N, K70R, T215Y) in assay with and without 3.2 mM ATP.

The degree of resistance shown by the 41/67/70/215 mutant is expressed as an increase of $K_i/K_m$ value compared to the wild type corresponding ratio (Table 2.). In the absence of added ATP or PPi the 41/67/70/215 mutant had lower $K_i$ and $K_m$ values than the wild type RT. The mutant $K_i/K_m$ ratio was 0.9 when divided by the equivalent ratio derived for wild type RT. (Table 2.). This apparent lack of biochemical resistance is consistent with previous studies of AZT mutants using conventional RT assays. Lacey, S. F. et al. *J. Biol. Chem.* 267, 15789–15794(1992). However, the inclusion of physiological concentrations of ATP (3.2 mM) dramatically increased this resistance to 16.6-fold. This degree of resistance was now similar to the 24-fold resistance seen with the HIV drug susceptibility assay (Table 1.).

The effect of PPi (150 μM) on AZT-TP inhibition was also tested. An increase in $K_i$ was seen for both wild type and mutant, however, the mutant was 10.5-fold more resistant relative to wild type (Table 2.). To ensure that the previous effect seen by ATP was not influenced by PPi contamination, a control experiment was conducted where the ATP reagent was pretreated with pyrophosphatase. No significant difference in fold resistance for mutant towards wild type was seen between treated and untreated ATP. The slightly lower $K_i$ and $K_m$ values were probably due to a different buffer used or the harsh temperature treatment of ATP, as the ATP effect is depended on the concentration used (see results with 1.5 and 6 mM ATP). The highest resistance level for the 41/67/70/215 mutant was found with 3.2 mM ATP. When ATP (3.2 mM) combined with PPi (150 μM) was studied, both wild type and 41/67/70/215 mutant showed a large increase in $K_i$ and $K_m$ values, but the level of resistance for the 41/67/70/215 mutant (12.6 fold) was lower compared with 3.2 mM ATP alone (16.6 fold) (Table 2.).

To evaluate the effect of GTP and PPi in the RT assay, three RT mutants, 41/67/70/215, 41/215 and 69S-AG, were selected and compared with the wild type enzyme. Using GTP at intracellular concentrations (0.5 mM) no significant increase in the level of resistance was obtained for any of the studied mutants (1.2–1.3 fold), the value for 41/67/70/215

TABLE 2

Comparison of AZT susceptibility of wild type and the 41/67/70/215 RT mutant in AZT-TP inhibition assay systems.

| Extra additions in RT AZT-TP assay | HXB2 $K_i$ (nM) | $K_m$ (nM) | $K_i/K_m$ | 41/67/70/215 mutant $K_i$ (nM) | $K_m$ (nM) | $K_i/K_m$ | Fold resistance in RT-assay relative to HXB2 |
|---|---|---|---|---|---|---|---|
| None | 5.8 | 170 | 0.034 | 0.3 | 10 | 0.03 | 0.9 (+/−0.1) |
| ATP (1.5 mM) | 4.8 | 240 | 0.02 | 6.4 | 64 | 0.1 | 5.0 (+/−1) |
| ATP (3.2 mM) | 10 | 310 | 0.032 | 39 | 74 | 0.53 | 16.6 (+/−0.3) |
| ATP (6.0 mM) | 40 | 810 | 0.049 | 176 | 225 | 0.78 | 15.9 (+/−4) |
| GTP (0.5 mM) | 9 | 324 | 0.028 | 4 | 117 | 0.034 | 1.2 (+/−0.03) |
| PPi (150 μM) | 26 | 300 | 0.087 | 83 | 90 | 0.92 | 10.5 (+/−3) |
| Pyrophosphatase treated ATP (3.2 mM) | ND | ND | ND | 16* | 37* | 0.42* | ND |
| Nontreated pyrophosphatase ATP (3.2 mM) | ND | ND | ND | 20* | 44* | 0.46* | ND |
| ATP (3.2 mM) + PPi (150 μM) | 59 | 517 | 0.11 | 280 | 202 | 1.39 | 12.6 (+/−3) |

The wild type HXB2 (two batches) and mutant RT was purified and studied in the RT assay. $K_i$ and $K_m$ values were calculated in the presence of ATP, GTP or/and PPi. $K_i$ values are expressed as concentration of AZT-TP. Three different concentrations of AZT-TP were used and were adapted to respective HXB2 or mutant $K_i$ values; 15, 40 and 100 nM for 41/67/70/215 mutant with 1.5 and 3.2 mM ATP or PPi and HXB2 with 6 mM ATP, and 3.2 mM ATP plus PPi; 40 100 and 250nM for 41/67/70/215 mutant with 6 mM ATP, and 3.2 mM ATP plus PPi; 5, 15 and 40 nM for all others. $K_m$ values are expressed as concentration of BrdUTP. Fold resistance (in boldface) is the $K_i/K_m$ ratio of the values divided by the equivalent ones for wild type RT. All values are averages calculated from at least two separate experiments except * marked, which were a single experiment. ND, not determined.

mutant is displayed in Table 2. When 150 µM PPi was included, a 10.5 and 3.3 level of resistance was obtained for 41/67/70/215 (Table 2.) and the 69S-AG mutant, respectively. There was no increase in resistance with PPi for the 41/215 mutant (1.1 fold).

EXAMPLE 2

Mutations Involved in the of Resistance of HIV-1 to Zidovudine (AZT)

Figure 2:
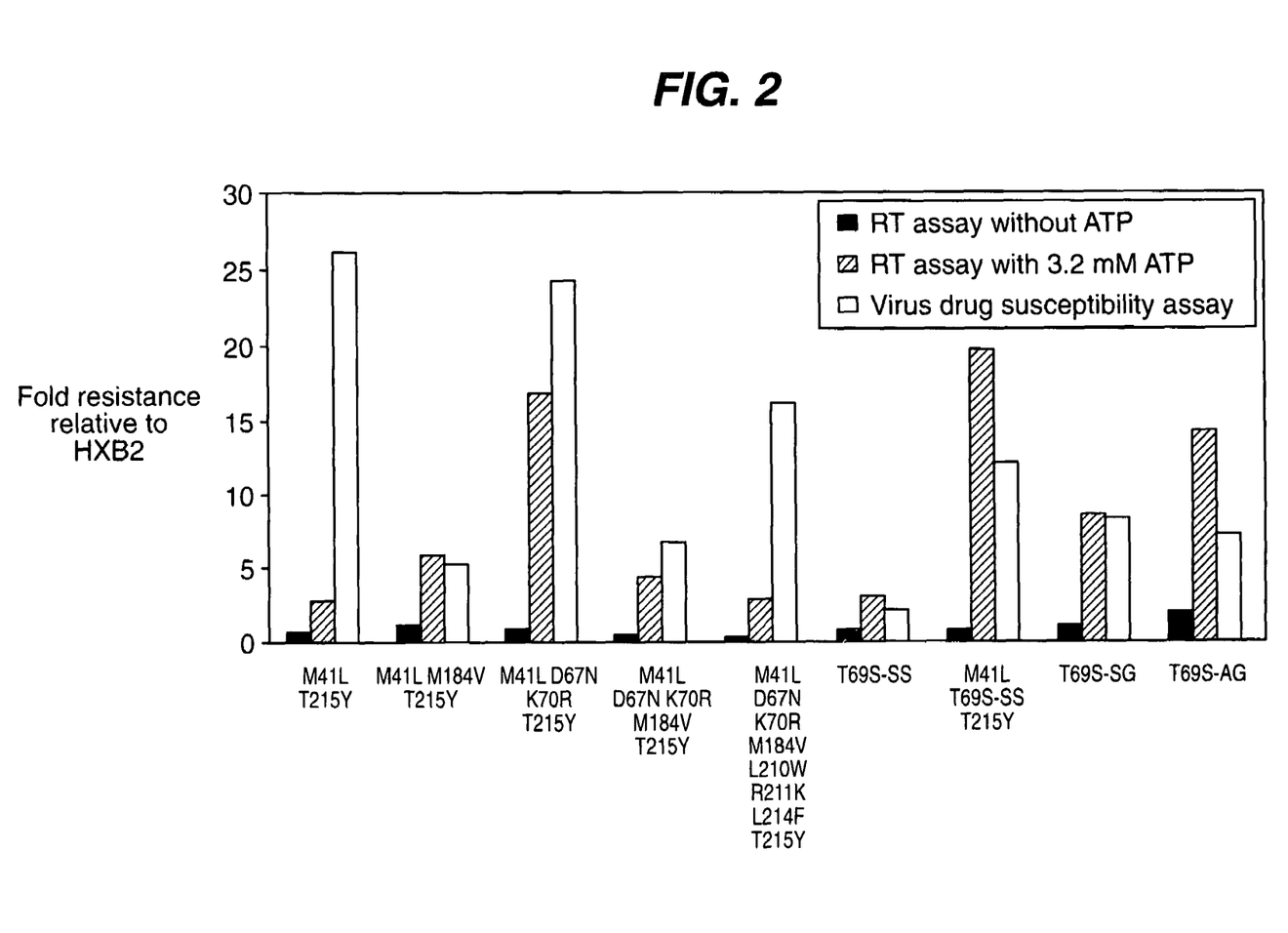

The RT assay of the present invention was next used to investigate which mutation sites are involved in the AZT resistance mechanism. Eight site-directed mutant RTs (see Table 1.) together with the 41/67/70/215 mutant and wild type RT were studied with and without the addition of ATP. The data are illustrated in Table 3. and FIG. 2.

sponding viral resistance data. The lowest resistance was as expected seen for the 69S-SS mutant and the highest (20-fold) for the 41/69S-SS/215 mutant. When assessing the data from the RT assay with ATP compared with the virus inhibition data (phenotypic data) (FIG. 1.), we found a better linear regression fit for the mutants that contained changes either at codons 67 and 70, or 69 (i.e. thereby excluding mutants 41/215 and 41/184/215) (y=0.5x+6, r=0.5, n=7), compared with all the mutants (y=0.2x+10, r=0.15, n=9). By further excluding M184V mutants 41/67/70/184/215 and 41/67/70/184/210/211/214/215 an even better linear regression fit was observed (y=0.9x+0.1, r=0.7, n=5).

The RT assay demonstrated at the enzyme level the AZT resistance reversal effect of the M184V mutation on AZT resistance mutations. The clearest effect of M184V is seen for enzymes containing the 67/70 AZT resistance mutations.

TABLE 3

AZT resistance of RT mutants and wild type measured with the AZT-TP inhibition assay with or without 3.2 mM ATP and by HIV-1 drug susceptibility assay.

| Genotype | RT AZT-TP assay without ATP | | | | RT AZT-TP assay with 3.2 mM ATP | | | | Virus Assay fold resistance |
|---|---|---|---|---|---|---|---|---|---|
| | $K_i$ (nM) | $K_m$ (nM) | $K_i/K_m$ | Fold resistance | $K_i$ (nM) | $K_m$ (nM) | $K_i/K_m$ | Fold resist. with ATP | |
| Wildtype (HXB2) | 5.8 | 170 | 0.034 | 1.0 (+/−0.06) | 10 | 310 | 0.032 | 1.0 (+/−0.09) | 1.0 |
| 41/215 | 3 | 110 | 0.027 | 0.8 (+/−0.08) | 34 | 360 | 0.094 | 2.9 (+/−0.1) | 26.2 (+/−10) |
| 41/184/215 | 2.2 | 49 | 0.045 | 1.3 (+/−0.3) | 26 | 140 | 0.19 | 5.9 (+/−0.2) | 5.2 (+/−1.5) |
| 41/67/70/215 | 0.3 | 10 | 0.03 | 0.9 (+/−0.1) | 39 | 74 | 0.53 | 16.6 (+/−0.3) | 24.1 (+/−14) |
| 41/67/70/184/215 | 0.6 | 60 | 0.01 | 0.3 (+/−0.2) | 50 | 380 | 0.13 | 4.1 (+/−0.0) | 6.4 (+/−1.5) |
| 41/67/70/184/210/211/214/215 | 1.3 | 120 | 0.011 | 0.3 (+/−0.0) | 52 | 580 | 0.09 | 2.8 (+/−0.05) | 16.0 (+/−2) |
| 69S-SS | 1.7 | 66 | 0.026 | 0.8 (+/−0.1) | 21 | 220 | 0.095 | 3.0 (+/−0.8) | 2.0 (+/−1) |
| 41/69S-SS/215 | 1.4 | 45 | 0.031 | 0.9 (+/−0.05) | 133 | 210 | 0.63 | 19.7 (+/−6) | 12.0 (+/−2) |
| 69S-SG | 3.8 | 100 | 0.038 | 1.1 (+/−0.1) | 96 | 360 | 0.27 | 8.4 (+/−3) | 8.1 (+/−4) |
| 69S-AG | 6.4 | 100 | 0.064 | 1.9 (+/−0.1) | 125 | 280 | 0.45 | 14.0 (+/−1) | 7.0 (+/−4) |

The RT AZT-TP assays $K_i$ and $K_m$, and fold resistance (highlighted) values were calculated as described in legend to Table 2 and Material and Methods. The virus AZT assay fold resistance values are based on $IC_{50}$ relative to wild type HXB2 virus control. The mean $IC_{50}$ of AZT for the wild type control virus was 0.012 µM. All values are the average calculated from at least two separated experiments.

In the absence of ATP, all the mutants behaved in a similar way to wild type RT (0.3–1.9-fold resistance) and no correlation with the virus inhibition data (phenotypic data) was seen. By contrast, reasonable correlation was observed between the virus inhibition data (phenotypic data) and the RT assay of the present invention when 3.2 mM ATP was included.

However, there were two apparent exceptions. Firstly, only 3-fold resistance was seen for the 41/215 mutant and there was also lower resistance compared to the drug susceptibility assay for the 41/67/70/184/210/211/214/215 mutant. The AZT-TP susceptibility of the latter M184V-containing mutant was similar to the modest RT resistance seen with the other M184V mutants (41/184/215 and 41/67/70/184/215). The 69 insertions all matched well with the virus assay level of resistance; in these cases the biochemical resistance was slightly higher overall than the corresponding viral resistance data. This suggests that the M184V mutation causes such reversion through interactions with these residues in the β2–β3 loop of RT.

To summarize, the novel methods of the invention elucidated the mechanism of AZT-TP resistance. The novel RT assay was, with one exception, consistent with virus assay data (Table 3., FIG. 2.). In conclusion, we have demonstrated a close correlation between virus AZT resistance and resistance to AZT-TP at the RT enzyme level. This is the first time that this has been studied with a group of AZT resistant mutants. This mechanism of removal of incorporated AZT-MP was found to depend on both ATP and PPi at presumed physiological concentrations.

Without the addition of ATP, GTP or pyrophosphate, all HIV mutant enzymes behaved as wild type enzymes. The addition of 3.2 mM ATP generally resulted in measurable resistance at the RT level that correlated well with the virus assay. Pyrophosphate (150 µM) in place of ATP in the RT assay resulted in approximately two-fold lower resistance values. The AZT resistant mutations D67N and K70R, and insertions T69-SG and T69S-AG, found in the RT 'fingers' domain were involved in the ATP dependent mechanism. Furthermore, the M184V mutation reversed the effect of the D67N and K70R mutations in this biochemical assay system, which was similar to the effect seen in the virus assay.

EXAMPLE 3

Mechanism of Resistance of HIV-1 to Stavudine (d4T)

The biochemical mechanism of HIV-1 resistance to d4T is also unclear and quite puzzling. For example, the incidence of phenotypic resistance to d4T in patient samples is moderate as compared to most other nucleoside analogs, such as AZT. Additionally, while high levels of d4T resistance are rarely found, viruses with reduced levels of d4T sensitivity are found to be to be cross resistant to other nucleoside analogs rather than possessing specific d4T resistance. Therefore, a clear understanding of d4T resistance should be helpful in understanding multi-drug resistant HIV mutations and aid in the design of drugs that are effective against these HIV strains.

Using the methods described in Example 1, various site directed HIV-1 RT mutants that are known or suspected to confer reduced d4T susceptibility were constructed (Table 1). The d4T susceptibility of these mutants relative to wild type HIV virus (HXB2) was then studied in both a recombinant virus assay (phenotypic assay) and the RT assay described in Example 1, i.e. an enzymatic kinetics assay. The level and mechanism of HIV resistance to d4T and d4T-TP, at the enzyme level, was examined with and without physiological concentrations of ATP.

Figure 3:
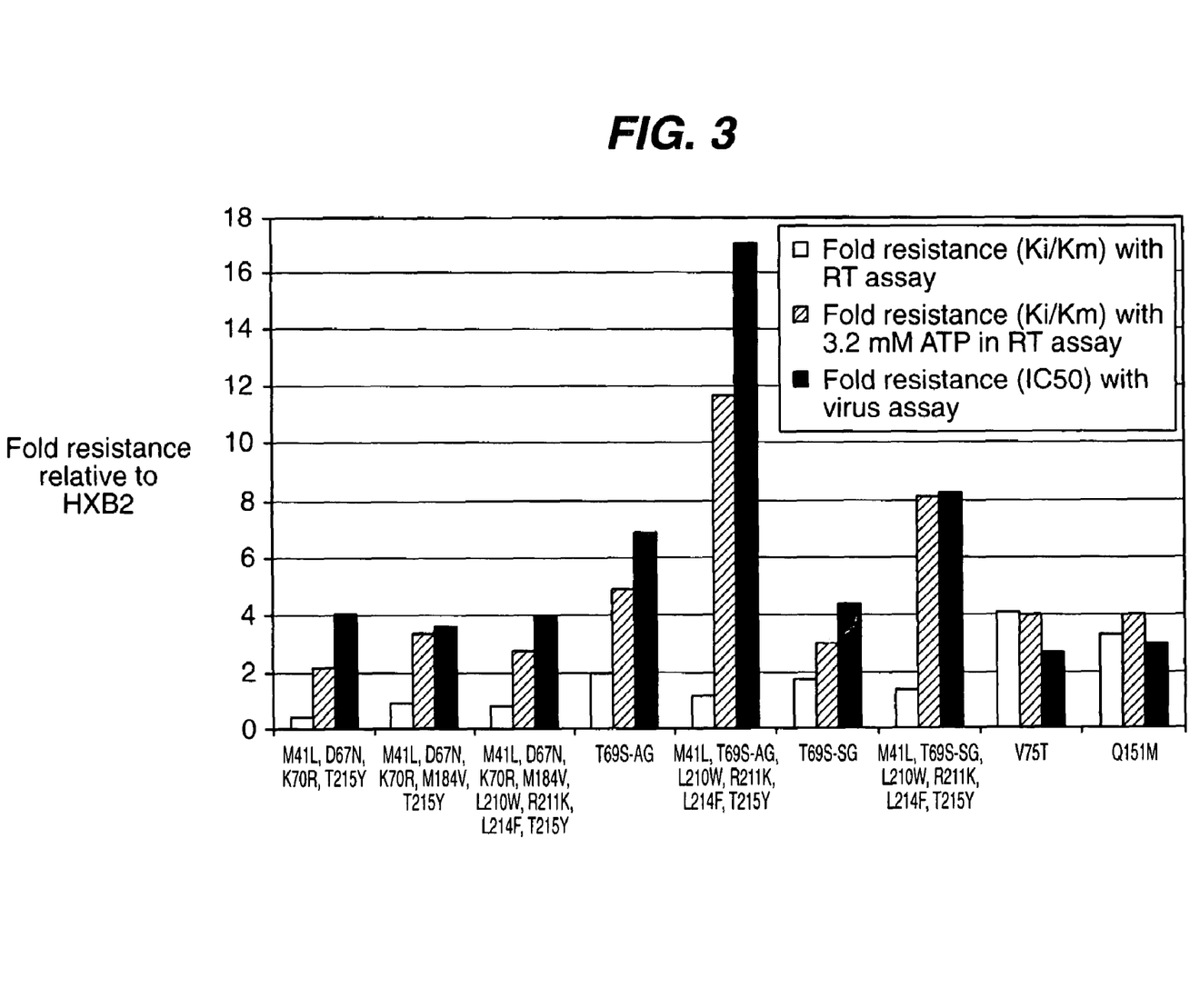

The kinetic data for d4T-TP resistance that was obtained using the RT assay is shown in Table 4 and FIG. 3.

The in vitro identified d4T specific mutation 75T and the multidrug resistant mutation 151M exhibited modest reduced d4T sensitivity. However, unlike for AZT resistance, the RT assay with and without ATP correlates with the virus assay (phenotypic data). Therefore, these mutations appear to be involved in decreased binding to d4T-TP independently of ATP.

When these mutants were tested in the RT assay for resistance to AZT-TP, similar ATP and non-ATP dependency was found. Consequently, the mutations involved in d4T resistance seem to overlap with, and have a similar mechanism as, AZT or multidrug mutations. However, in most cases d4T resistance is the lower resistance.

All references, patents, and patent application cited herein are incorporated by reference in their entirety.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for determining the AZT susceptibility of a test HIV-1 RT enzyme, comprising:
   a) providing a reaction well with the following reaction components comprising:
      i. at least one template for an HIV-1 RT enzyme;
      ii. at least one primer;
      iii. at least one detectable dNTP substrate;
      iv. AZT; and
      v. at least one compound chosen from ATP at a final concentration in the range of from about 1.5 mM to about 6 mM in the reaction well or pyrophosphate at about the physiological concentration in the reaction well;
   b) performing an enzymatic kinetics assay by adding to the reaction well the test HIV-1 RT enzyme;

TABLE 4 d4T resistance of RT mutants and wild type measured with d4T-TP inhibition assay with or without 3.2 mM ATP and by HIV-1 drug susceptibility assay (Virus Assay).

| | RT assay without ATP | | | % Vmax with ATP | RT assay with 3.2 mM ATP | | | Virus Assay |
|---|---|---|---|---|---|---|---|---|
| Mutations | $K_i$ (nM) | $K_m$ (nM) $K_i/K_m$ | Fold resistance | relative to without ATP | $K_i$ (nM) | $K_m$ (nM) $K_i/K_m$ | Fold resistance with ATP | Anivirogram Fold resistance |
| Wild Type (HXB2) | 1.1 | 136  0.0081 | 1.0 +/− 0.1 | −33% | 1.6 | 162  0.01 | 1.0 +/− 0.1 | 1.0 |
| M41L, D67N, K70R, T215Y | 0.3 | 80  0.004 | 0.5 | −31% | 2.8 | 126  0.022 | 2.2 | 4.1 +/− 1.3 |
| M41L, D67N, K70R, M184V, T215Y | 0.6 | 75  0.008 | 1.0 | −14% | 5.2 | 152  0.034 | 3.4 | 3.7 +/− 1.0 |
| M41L, D67N, K70R, M184V, L210W, R211K, L214F, T215Y | 1.5 | 216  0.007 | 0.9 | −37% | 6.9 | 249  0.028 | 2.8 | 4.0 +/− 1.3 |
| T69S-AG | 1.9 | 117  0.016 | 2.0 +/− 0.4 | −31% | 6.2 | 126  0.049 | 4.9 +/− 0.2 | 6.9 +/− 2.7 |
| M41L, T69S-AG, L210W, R211K, L214F, T215Y | 1.3 | 130  0.01 | 1.2 +/− 0.3 | −26% | 27.0 | 230  0.117 | 11.7 +/− 1.4 | 17.1 +/− 0.6 |
| T69S-SG | 3.7 | 239  0.015 | 1.8 +/− 0.2 | −35% | 6.8 | 228  0.03 | 3.0 +/− 0.6 | 4.4 +/− 1.1 |
| M41L, T69S-SG, L210W, R211K, L214F, T215Y | 0.9 | 83  0.011 | 1.4 | −25% | 14.7 | 184  0.08 | 8.1 | 8.3 +/− 1.8 |
| V75T | 2.6 | 79  0.033 | 4.1 +/− 0.6 | −24% | 6.6 | 165  0.04 | 4.0 +/− 0.6 | 2.7 +/− 0.4 |
| Q151M | 3.0 | 117  0.026 | 3.3 +/− 0.9 | −19% | 7.1 | 174  0.04 | 4.0 +/− 0.1 | 3.0 +/− 0.8 | c) measuring the amount of the detectable dNTP substrate bound to the template;

d) repeating steps a) through c), replacing the test HIV-1 RT enzyme with a control HIV-1 RT enzyme that is known to be susceptible to AZT inhibition; and e) comparing the amount of the detectable dNTP substrate measured from step c) with that from step d);

wherein the test HIV-1 RT enzyme is identified to be AZT resistant when the amount of the detectable dNTP substrate measured from step c) is more than that from step d); and the test HIV-1 RT enzyme is identified to be AZT susceptible when the amount of the detectable dNTP substrate measured from step c) is less than or equal to that from step d).

2. The method of claim 1, wherein the template is bound to the reaction well and is chosen from poly-rA or a heteropolymer RNA or DNA.

3. The method of claim 1, wherein the primer is chosen from oligo-dt or a primer that is complementary to the heteropolymer template.

4. The method of claim 1, wherein the detectable dNTP substrate is chosen from a radioactive labeled dNTP.

5. The method of claim 1, wherein the detectable dNTP substrate is capable of being detected by fluorescence, luminescence, or absorption spectrometry.

6. The method of claim 1, wherein the detectable dNTP substrate binds to an optical tracer or a radioactive labeled tracer.

7. The method of claim 6, wherein the optical tracer is capable of being detected by fluorescence, luminescence, or absorption spectrometry.

8. The method of claim 6, wherein the detectable dNTP precursor is bromo-deoxyuridine-triphosphate.

9. The method of claim 8, wherein the optical tracer is a monoclonal anti-BrdU antibody, conjugated to alkaline phosphatase.

10. A method for identifying at least one mutation in an HIV-1 RT enzyme that increases or decreases the AZT susceptibility of the HIV-1 RT enzyme, comprising:

a) providing a reaction well with the following reaction components comprising:
  i. at least one template for an HIV-1 RT enzyme;
  ii. at least one primer;
  iii. at least one detectable dNTP substrate;
  iv. AZT; and
  v. at least one compound chosen from ATP at a final concentration in the range of from about 1.5 mM to about 6 mM in the reaction well, or pyrophosphate at about the physiological concentration in the reaction well;

b) performing an enzymatic kinetics assay by adding to the reaction well a HIV-1 RT enzyme;

c) determining RT activity by measuring the amount of the detectable dNTP substrate bound to the template;

d) repeating steps a) through c), replacing the HIV-1 RT enzyme with a mutant HIV-1 RT enzyme comprising at least one mutation, wherein the mutant HIV-1 RT enzyme is otherwise identical to the HIV-1 RT enzyme except for the at least one mutation; and e) comparing the amount of the detectable dNTP substrate measured from step c) with that from step d);

wherein the at least one mutation increases the AZT susceptibility of the HIV-1 RT enzyme when the amount of the detectable dNTP substrate measured from step c) is more than that from step d); and the at least one mutation decreases the AZT susceptibility of the HIV-1 RT enzyme when the amount of the detectable dNTP substrate measured from step c) is less than that from step d).

11. A method for rapid screening of mutations in an HIV-1 RT enzyme that increase or decrease the AZT susceptibility of the HIV-1 RT enzyme, comprising:

a) providing an array of reaction wells, each reaction well with the following reaction components comprising:
  i. at least one template for an HIV-1 RT enzyme;
  ii. at least one primer;
  iii. at least one detectable dNTP substrate;
  iv. AZT; and
  v. at least one compound chosen from ATP at a final concentration in the range of from about 1.5 mM to about 6 mM in the reaction well or pyrophosphate at about the physiological concentration in the reaction well;

b) performing an enzymatic kinetics assay by adding to each reaction well a RT enzyme chosen from an HIV-1 RT enzyme or a mutant HIV-1 RT enzyme comprising at least one mutation, wherein the mutant HIV-1 RT enzyme is otherwise identical to the HIV-1 RT enzyme except for the at least one mutation;

c) in each reaction well measuring the amount of the detectable dNTP substrate bound to the template; and d) comparing the amount of the detectable dNTP substrate measured from the well containing the mutant HIV-1 RT enzyme with that from the well containing the HIV-1 RT enzyme;

wherein mutations that increase or decrease the AZT susceptibility of the HIV-1 RT enzyme are rapidly identified.

12. The method of claim 1, wherein the control RT enzyme in step d) is a wild-type HIV-1 RT enzyme.

13. The method of claim 10, further comprising the steps of:

f) repeating step d) of the method of claim 10, omitting the at least one compound chosen from ATP at a final concentration in the range of from about 1.5 mM to about 6 mM in the reaction well or at pyrophosphate at about the physiological concentration in the reaction well;

g) comparing the amount of the detectable dNTP substrate measured from step
  f) with that from step c) of claim 10, and with that from step d) of claim 10; wherein the at least one test mutation can be resistant to other HIV inhibitor(s) in addition to AZT when the amount of the detectable dNTP substrate measured from step f) is more than that from step c) of claim 10, and is substantially the same as that from step d) of claim 10.

14. The method of claim 1, wherein the ATP is at about the physiological concentration in the reaction well.

15. The method of claim 14, wherein the ATP is at a final concentration of about 3.2 mM in the reaction well.

16. The method of claim 1, wherein the pyrophosphate is at a final concentration of about 150 μM in the reaction well.

* * * * *